(12) United States Patent
Sutherland

(10) Patent No.: US 10,874,958 B1
(45) Date of Patent: Dec. 29, 2020

(54) CONTROLLING HEAT FLUX DURING DISTILLATION AND CONCENTRATION OF EXTRACT

(71) Applicant: ExtractCraft, LLC, Longmont, CO (US)

(72) Inventor: Lee Sutherland, Longmont, CO (US)

(73) Assignee: ExtractCraft, LLC, Longmont, CO (US)

( * ) Notice: Subject to any disclaimer, the term of this patent is extended or adjusted under 35 U.S.C. 154(b) by 0 days.

(21) Appl. No.: 16/554,281

(22) Filed: Aug. 28, 2019

Related U.S. Application Data

(62) Division of application No. 15/936,028, filed on Mar. 26, 2018, now Pat. No. 10,427,067.

(51) Int. Cl.
 *B01D 3/42* (2006.01)
 *C07C 29/84* (2006.01)
 *B01D 3/10* (2006.01)
 *B01D 3/02* (2006.01)

(52) U.S. Cl.
 CPC .............. *B01D 3/42* (2013.01); *B01D 3/02* (2013.01); *B01D 3/10* (2013.01); *C07C 29/84* (2013.01)

(58) Field of Classification Search
 CPC .... B01D 3/02; B01D 3/10; B01D 3/42; C07C 29/84
 See application file for complete search history.

(56) References Cited

U.S. PATENT DOCUMENTS

| 2,577,615 | A | 12/1951 | Garrison et al. |
| 4,962,270 | A | 10/1990 | Feimer et al. |
| 5,620,728 | A | 4/1997 | Langley et al. |
| 7,976,699 | B2 | 7/2011 | Kesler |
| 8,206,557 | B2 | 6/2012 | Burke et al. |
| 9,649,349 | B1 * | 5/2017 | Tucker ................... A61K 31/05 |
| 9,732,009 | B2 | 8/2017 | Raber et al. |
| 2008/0173531 | A1 | 7/2008 | Kesler |
| 2015/0209688 | A1 | 7/2015 | Young et al. |
| 2016/0280734 | A1 * | 9/2016 | Moore ..................... B01J 14/00 |

OTHER PUBLICATIONS

ExtractCraft.com "Source Turbo Mode User Manual (2017)"; downloaded May 18, 2019 from http://web.archive.org/web/20171110221845//http://www.ExtractCraft.com/s/Source-Turbo-Manual-V7.pdf.
McCaig, Brian; USPTO Office Action for U.S. Appl. No. 15/936,028; dated Jun. 19, 2019.
Thomas, Shane; International Search Report for International Patent Application No. PCT/US2019/23974, dated Jun. 11, 2019, 4 pages.
Thomas, Shane; Written Opinion for International Patent Application No. PCT/US2019/23974, dated Jun. 11, 2019, 16 pages.

* cited by examiner

*Primary Examiner* — Brian A Mccaig
(74) *Attorney, Agent, or Firm* — MP Patents, LLC

(57) ABSTRACT

A method for phytochemical extraction includes providing a distillation vessel, providing a mixture of solvent and plant extract to the distillation vessel, placing the distillation vessel on a heat source, coupling the distillation vessel with a collector configured to collect condensed solvent, selecting an initial distillation temperature and outputting heat from the heat source at a heat source initial target temperature to heat the distillation vessel to a distillation vessel initial target temperature and boil the mixture in the distillation vessel at the initial distillation temperature and at an initial heat flux. With a vacuum pump, a distillation vessel initial target pressure is set within the distillation vessel.

21 Claims, 4 Drawing Sheets

CONTROLLING HEAT FLUX DURING DISTILLATION AND CONCENTRATION OF EXTRACT

CROSS-REFERENCE TO RELATED APPLICATIONS

This application is a Divisional Application of and incorporates by reference in its entirety U.S. NonProvisional application Ser. No. 15/936,028 filed Mar. 26, 2018 and entitled CONTROLLING HEAT FLUX DURING DISTILLATION AND CONCENTRATION OF EXTRACT'.

SUMMARY

The present disclosure describes a method for phytochemical extraction. The method includes providing a distillation vessel, placing the distillation vessel on a heat source, coupling the distillation vessel with a collector configured to collect condensed solvent, providing a mixture of solvent and plant extract to the distillation vessel, selecting an initial distillation temperature, outputting heat from the heat source at a heat source initial target temperature to heat the distillation vessel to a distillation vessel initial target temperature and boil the mixture in the distillation vessel at the initial distillation temperature and at an initial heat flux and initial distillation rate and, with a vacuum pump, setting a distillation vessel initial target pressure within the distillation vessel.

The present disclosure describes another method for phytochemical extraction which includes providing a distillation vessel, coupling the distillation vessel with a collector configured to collect condensed solvent, providing a mixture of solvent and plant extract to the distillation vessel, selecting an initial distillation temperature, outputting heat from the heat source at a heat source initial target temperature to heat the distillation vessel to a distillation vessel initial target temperature and boil the mixture in the distillation vessel at the initial distillation temperature and at an initial heat flux and distillation rate and, with a vacuum pump, setting a distillation vessel initial target pressure within the distillation vessel. The method further includes in response to selection of a modified distillation temperature different from the initial distillation temperature, changing the heat output from the heat source and the pressure set with the vacuum pump to boil the mixture in the distillation vessel at the modified distillation temperature while maintaining the initial heat flux.

The present disclosure describes another method for phytochemical extraction which includes providing a distillation vessel, coupling the distillation vessel with a heat source, coupling the distillation vessel with a collector configured to collect condensed solvent, providing a mixture of solvent and plant extract to the distillation vessel, selecting an initial distillation temperature, outputting heat from the heat source at a heat source initial target temperature to heat the distillation vessel to a distillation vessel initial target temperature and boil the mixture in the distillation vessel at the initial distillation temperature and at an initial heat flux and distillation rate and, with a vacuum pump, setting a distillation vessel initial target pressure within the distillation vessel. The method further includes in response to selection of a modified distillation temperature different from the initial distillation temperature, changing the heat output from the heat source and the pressure set with the vacuum pump to boil the mixture in the distillation vessel at the modified distillation temperature while maintaining avoiding eruptive boiling.

BRIEF DESCRIPTION OF THE FIGURES

The summary above, as well as the following detailed description of illustrative embodiments, is better understood when read in conjunction with the appended figures. For the purpose of illustrating the present disclosure, example constructions of the disclosure are shown in the figures. However, the present disclosure is not limited to specific methods and instrumentalities disclosed herein. Moreover, those having ordinary in the art will understand that the figures are not to scale. Wherever possible, like elements have been indicated by identical numbers.

Embodiments of the present disclosure will now be described, by way of example only, with reference to the following diagrams wherein.

DETAILED DESCRIPTION

Figure 1:
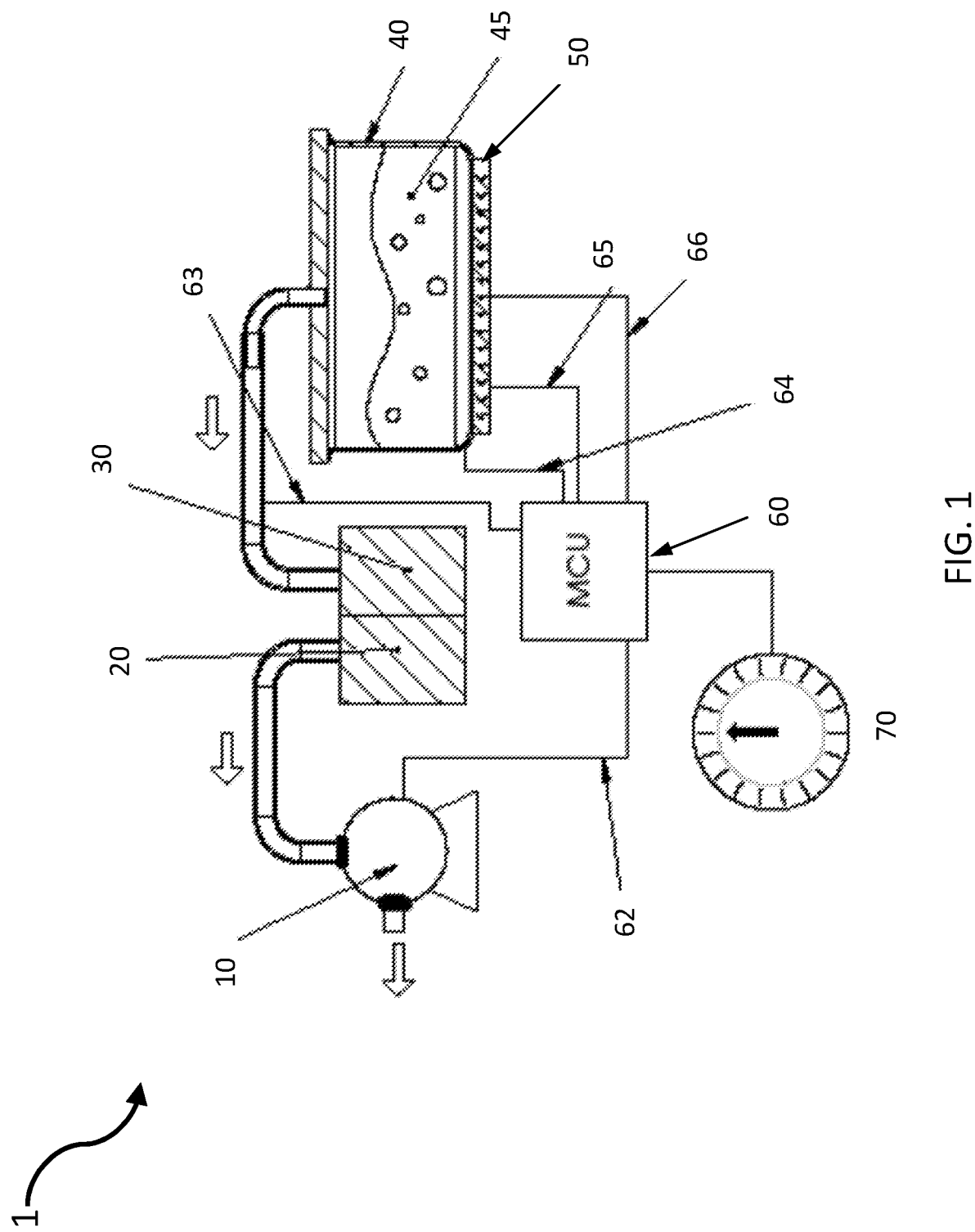
FIG. 1 illustrates an example system for phytochemical extraction.

The following detailed description illustrates embodiments of the present disclosure and manners by which they can be implemented. Although the best mode of carrying out the present disclosure has been described, those of ordinary skill in the art would recognize that other embodiments for carrying out or practicing the present disclosure are also possible.

It should be noted that the terms "first", "second", and the like, herein do not denote any order, quantity, or importance, but rather are used to distinguish one element from another. Further, the terms "a" and "an" herein do not denote a limitation of quantity, but rather denote the presence of at least one of the referenced item.

Solvent distillation for the extraction of plant phytochemicals is an important process for the food, beverage, flavorings, pharmaceuticals, and industrial chemical industries. Extracts of interest are removed from plant material by mixing the plants with solvent including, for example, alcohols such as ethanol or isopropanol. The liquid extract mixture is then filtered from the plant material and introduced into a distillation vessel, where the solvent is removed at a controlled temperature and reduced pressure until only the substantially pure plant extract remains in the vessel.

The temperature of the process is controlled to provide as high a heat flux into the vessel as possible to allow distillation to occur as rapidly as possible without exceeding temperatures that will induce thermochemical degradation that damages the extracted product. The distillation temperature of the solvent in the gross mixture varies with the molar concentration of the mixture and the absolute pressure inside the distillation vessel.

The temperatures typical for the concentration process for many extracts including *Cannabis* and culinary herbs are between 98 and 105 degrees Fahrenheit. Aromatic extracts can require significantly lower temperatures of between 80 to 100 degrees Fahrenheit.

Ideally, the maximum temperature in the extract mixture should not exceed the desired extract temperature, the mixture should not undergo eruptive boiling, and the heat flux should be maintained at a higher level to process more quickly even as the concentration of the extract in the mixture reaches its final, viscous state upon removal of alcohol. Some alcohols and other fluids with a relatively low enthalpy of vaporization coupled with other factors such as viscosity, density, and thermal conductivity tend to promote significant superheating in a heated vessel. This tendency will cause rapid eruptive boiling characterized by sudden large scale vapor release from the heated liquid. This may result in the extract mixture fouling the inside of the heated vessel, making containment and collection difficult as the concentration process progresses. The superheated temperatures can also be significantly higher than the bulk of the extract mixture, which can degrade the extract product.

Eruptive boiling can be reduced by decreasing the heat flux into the distillation vessel, vigorous stirring, or other means. Vigorous stirring and other means have significant disadvantages including but not limited to the need to introduce foreign objects into the mixture, making cleaning and use of the product difficult, or greatly slowing the distillation process.

The disclosed systems and methods promote regular, stable nucleate boiling in an ethanol extract mixture through careful control of heat flux into the distillation vessel to allow nucleation and homogeneous release of vapor from the heated surface of the distillation vessel.

Distillation temperature can be substantially continuously modulated while maintaining an optimally high heat flux, process speed and critical nucleate boiling characteristic with variable feedstocks. The excessive temperatures of a superheated extract mixture can be avoided while maintaining optimal heat flux for distillation of alcohol Additional aspects, advantages, features and objects of the present disclosure will be made apparent from the figures and the detailed description of the illustrative embodiments construed in conjunction with the appended claims that follow.

It will be appreciated that features of the present disclosure are susceptible to being combined in various combinations without departing from the scope of the present disclosure as defined by the appended claims.

FIG. 1 is a schematic illustration of various components of an example system 1 for phytochemical extraction, in accordance with an embodiment of the present disclosure.

With system 1, a vacuum distillation process may be undertaken at different temperatures to control product quality through the use of a microcontroller to regulate pressure and therefore the boiling temperature of a plant extract and solvent mixture. In conjunction, heat source temperature control maintains a constant heat flux regardless of the temperature setting to establish and maintain stable nucleate boiling characteristics of the extract mixture throughout the distillation process. An automated response is provided to user temperature input, removing the need to determine target temperatures and pressures separately.

System 1, also configured for controlling heat flux during distillation and concentration of plant extract, includes a distillation vessel 40, a heater or heat source 50, a vacuum pump 10, a solvent collector 20, a heat exchanger 30, a user input element 70, and a microcontroller 60.

Distillation vessel 40 is configured for containing a mixture 45 of solvent and plant extract and includes a heat transfer surface to be placed into thermal communication with a conductive portion of heat source 50. In an example, the distillation vessel 40 may further include a plurality of surface features suitable as nucleation sites for nucleate boiling of mixtures of extract and solvent.

Solvent collector 20 is configured for coupling with the distillation vessel 40 to receive solvent vaporized from any mixture 45 of solvent and plant extract in the distillation vessel 40. In an example, collector 20 may be coupled with distillation vessel 40 through, in part, heat exchanger 30. Heat exchanger 30 facilitates condensation of vaporized solvent flowing between distillation vessel 40 and solvent collector 20.

Heat source 50 is configured for heating the heat transfer surface of the distillation vessel 40 and any mixture 45 of solvent and plant extract contained therein.

Vacuum pump 10 is configured for adjusting pressure in the distillation vessel 40.

Microcontroller 60 is configured to, in response to selection of an initial distillation temperature with the user input element 70, control the heat source 50 to output heat at a heat source initial target temperature to heat the distillation vessel 40 to a distillation vessel initial target temperature and an initial heat flux and control the vacuum pump 10 to set a distillation vessel initial target pressure within the distillation vessel 40.

User input element 70 is configured for signalling a user-selected distillation temperature to the microcontroller 60 to operate the vacuum pump 10 and adjust output of the heat source 50 to change distillation temperature while maintaining a constant heat flux between the distillation vessel 40 and any mixture 45 of solvent and plant extract contained therein. In an example, the user input element 70 enables substantially continuously variable user-selected distillation temperature.

Microcontroller 60 may include, but is not limited to a memory, a computing hardware such as a processor, and general purpose input/output pins. General purpose input/output pins may be configured to provide control output pins 62 and 66 as well as sensor input pins 63, 64, 65. A user input element 70 may be operatively coupled with one or more input/outputs of the microcontroller. Microprocessor 60 and input/outputs may be configured with one of various forms of programming.

The memory optionally includes non-removable memory, removable memory, or a combination thereof. The non-removable memory, for example, include flash memory. The removable memory, for example, includes flash memory cards, memory sticks, or smart cards.

The memory is configured for storing one or more look-up tables and programming for controlling one or more pumps and one or more heat sources of system 1 in response to input from sensors through pins 63, 64 and 65.

Microprocessor 60 is also provided with a power source for supplying electrical power to the various components thereof. The power source may, for example, include a rechargeable battery.

In an example, user input element 70 may be a touch-sensitive display screen operable to receive tactile inputs from the user. These tactile inputs may, for example, include clicking, tapping, pointing, moving, pressing and/or swiping with a finger or a touch-sensitive object like a pen.

Additionally or alternatively, user input element 70 may include a mouse or a joystick that is operable to receive inputs corresponding to clicking, pointing, and/or moving a pointer object on a graphical user interface. User input element 70 may also include a keyboard that is operable to receive inputs corresponding to pushing certain buttons on the keyboard.

Additionally or alternatively, user input element 70 may include a microphone for receiving an audio input from the user, and a speaker may be provided to output audio.

Additionally or alternatively, user input element 70 may be arranged to enable variable, user-selected change of distillation temperature, for example, as a dial. A dial may be virtual such as for use with the above-mentioned touch-sensitive display screen, may be a physical dial or may a combination of these.

In an example, microcontroller 60 is configured to control the heat source 50 through heat source output pin 66 and to control the vacuum pump through a vacuum pump output pin 62.

Moreover, the pins 63, 64 and 65 may be provided with or coupled with one or more of: a pressure sensor and a temperature sensor. The pins 63, 64 and 65 may be used to measure and/or collect data related to conditions of distillation vessel 40, mixture 45, heat source 50, heat exchanger 30, collector 20 and/or pump 10.

The programming of microcontroller 60 may be interfaced with the sensors through pins 63, 64 and 65 such that, when executed on the processor, the programming resolves and integrates the outputs of the sensors into useful information about at least one of: conditions of distillation vessel 40, mixture 45, heat source 50, heat exchanger 30, collector 20 and/or pump 10.

In some examples, one or more input/output pins may be provided with or coupled to a timer for including time-stamps with data about conditions of system 1. Alternatively, the computing hardware may provide system time as reference for including the time-stamps.

Microcontroller 60 is configured to determine the heat source initial target temperature from the initial distillation temperature. In an example, microcontroller 60 returns the heat source initial target temperature from one or more look-up tables relating heat source temperature to distillation temperature.

Since there may be a temperature difference between mixture and a location on distillation vessel that is convenient for measuring vessel temperature, it may be useful to have a relation between the temperature of the mixture and the temperature of the distillation vessel. In a further example, microcontroller 60 is further configured to return the heat source initial target temperature from a look-up table relating heat source temperature to vessel temperature which is returned from a look-up table relating distillation vessel temperature to distillation temperature.

Microcontroller 60 is further configured to determine the distillation vessel initial target pressure from the initial distillation temperature. In an example, microcontroller 60 returns the vessel initial target pressure from a look-up table relating vessel pressure to distillation temperature.

During use of system 1 to extract phytochemicals and/or maintain a substantially constant heat flux, microcontroller 60 is configured to sense pressure of the distillation vessel 40 and, with the vacuum pump 10, remove pressure from the distillation vessel 40 when the sensed pressure of the distillation vessel 40 is above the distillation vessel initial target pressure. In an example, microcontroller 60 senses the pressure through vessel pressure input pin 63.

Microcontroller 60 is further configured to sense temperature of the distillation vessel 40 and turn the heat source 50 off when the sensed temperature of the distillation vessel 40 is above the distillation vessel initial target temperature. In an example, microcontroller 60 senses the temperature of distillation vessel 40 through distillation vessel temperature input pin 64.

Microcontroller 60 is further configured to sense temperature of the distillation vessel 40 and make a further determination about the heat source 50 when the sensed temperature of the distillation vessel 40 is below the distillation vessel initial target temperature. When the sensed temperature of the distillation vessel 40 and the sensed temperature of the heat source 50 are below or equal to the distillation vessel initial target temperature and the heat source initial target temperature, respectively, the heat source 50 is turned on.

Microcontroller 60 is further configured to sense temperature of the heat source 50 without input from a distillation vessel temperature sensor and turn the heat source 50 off when the sensed temperature of the heat source 50 is above the heat source initial target temperature. When sensed temperature of the heat source 50 is equal to or below the heat source initial target temperature, the microcontroller 60 is configured to turn heat source 50 on. In an example, microcontroller senses the temperature of heat source 50 through heat source temperature input pin 65.

Microcontroller 60 is configured to operate the vacuum pump 10 and the heat source 50 in accordance with signalling from the user input element 70 and a relation between temperature and pressure.

In response to selection of a modified distillation temperature with the user input element 70, microcontroller 60 is further configured to control the heat source 50 to output heat at a heat source modified target temperature to heat the distillation vessel 40 to a distillation vessel modified target temperature and boil the mixture 45 in the distillation vessel 40 at the modified distillation temperature and the initial heat flux, to determine a distillation vessel modified target pressure the modified distillation temperature and to control the vacuum pump 10 to set the distillation vessel modified target pressure within the distillation vessel 40. In an example, microcontroller 60 is configured to return the distillation vessel modified target pressure from a look-up table relating the distillation vessel initial target pressure to distillation temperature.

The heat source modified target temperature may be determined from the vessel modified target temperature, the distillation vessel modified target temperature may be determined from the modified distillation temperature and the distillation vessel modified target pressure may be determined from the modified distillation temperature.

In an example, the heat source modified target temperature may be returned from a look-up table relating heat source temperature to distillation vessel temperature, the distillation vessel modified target temperature may be returned from a look-up table relating distillation vessel temperature to distillation temperature and the distillation vessel modified target pressure may be returned from a look-up table relating distillation vessel pressure to distillation temperature.

Microcontroller 60 is further configured to sense pressure of the distillation vessel 40 and remove pressure from the distillation vessel 40 when the sensed pressure of the distillation vessel 40 is above the distillation vessel modified target pressure.

Microcontroller 60 is further configured to sense temperature of the distillation vessel 40 and turn the heat source 50 off when the sensed temperature of the distillation vessel 40 is above the distillation vessel modified target temperature, to sense temperature of the heat source 50 and turn the heat source 50 off when the sensed temperature of the heat source 50 is above the heat source modified target temperature, and to sense temperature of heat source 50 and turn the heat source 50 on when the sensed temperature of the heat source 50 is equal to or below the heat source modified target temperature.

In a further example, microcontroller 60 is configured to sense temperature of the distillation vessel 40 and temperature of heat source 50 and turn the heat source 50 on when the heat source temperature is equal to or below heat source modified target temperature and the sensed temperature of the distillation vessel 40 is equal to or below the modified distillation vessel target temperature.

In another embodiment, microcontroller 60 can be programmed to reduce heat flux in a distillation vessel as the process temperature is reduced to accommodate very viscous extract products that will transition to eruptive boiling at heat flux values typical of mixtures rich in the alcohol distillate at the start of the distillation process.

In another embodiment, the user can select a subcooled temperature for the mixture with very low temperatures near ambient room temperatures to allow very long term removal of trace amounts of solvent from an extract mixture at the end of the rapid distillation process.

FIG. 1 is merely an example, which should not unduly limit the scope of the claims herein. It is to be understood that the specific designations for system 1 and microcontroller 60 are provided as examples and are not to be construed as limiting system 1 or microcontroller 60 to specific numbers, types, or arrangements of modules and/or components. A person skilled in the art will recognize many variations, alternatives, and modifications of embodiments of the present disclosure.

Figure 2:
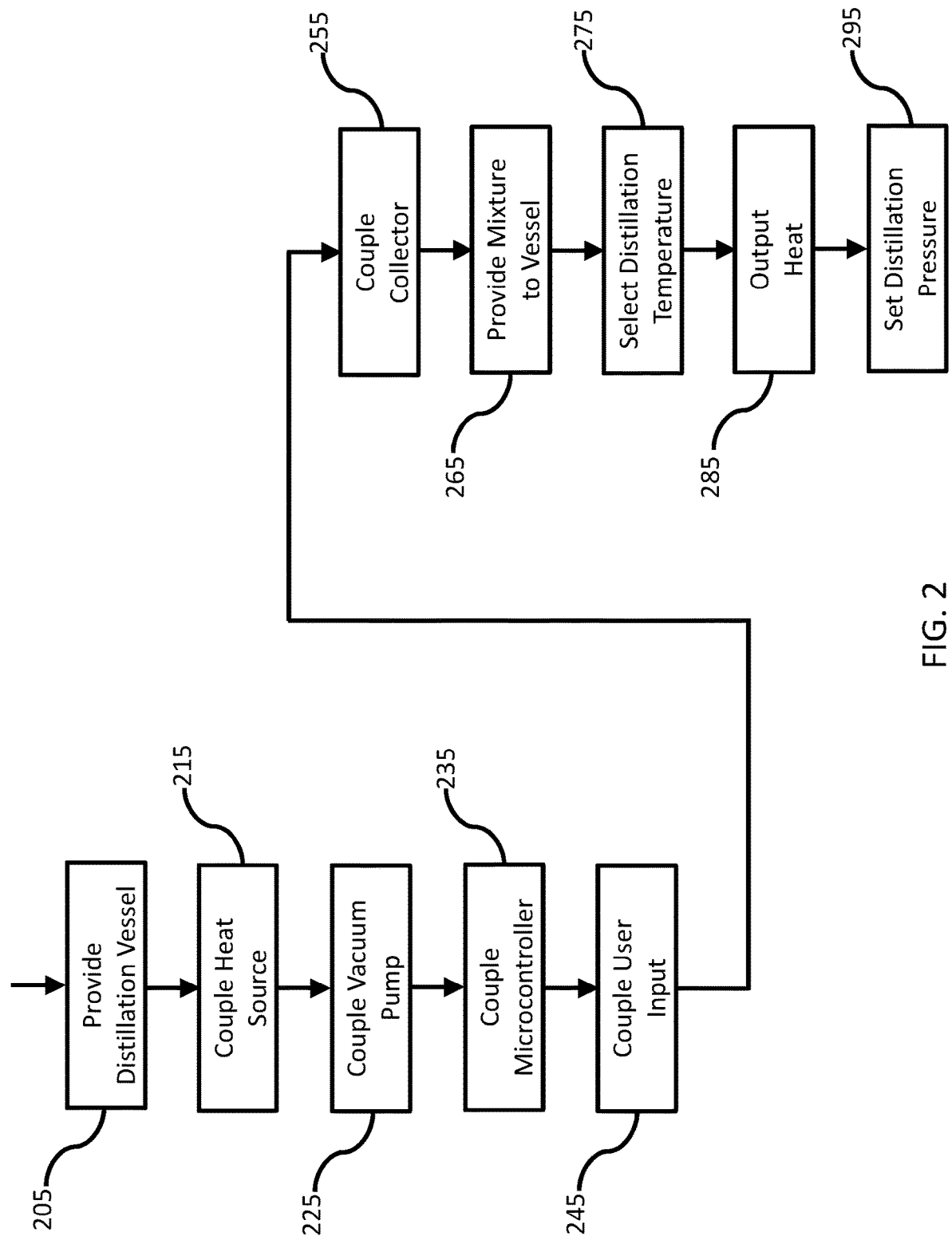
FIG. 2 illustrates a flow for an example method for phytochemical extraction.

FIG. 2 illustrates a flow for an example method for distillation and concentration of plant extract and/or phytochemical extraction with controlled heat flux. The method, which may for example be practiced with the above-described system, is depicted as a collection of actions in a logical flow diagram, which represents a sequence or actions that may be implemented in hardware, software, or a combination thereof.

A method for phytochemical extraction includes providing a distillation vessel at 205, coupling the distillation vessel to a heat source at 215 such that the heat source selectively heats the distillation vessel and any mixture of solvent and plant extract contained therein and coupling a vacuum pump to the distillation vessel at 225 such that vacuum pump selectively adjusts pressure in the distillation vessel. The distillation vessel provided may include surface features to enhance nucleation as described briefly above. Coupling the distillation vessel to a heat source may include simply placing the distillation vessel on the heat source and allowing gravity to hold it in place on the heat source or may include securing the distillation vessel on the heat source with one or more clamps, clips or grips. In another embodiment, a heat source may be coupled to a distillation vessel at a location other than the distillation vessel bottom.

A microcontroller is coupled to the heat source and vacuum pump at 235 and is configured for operating the vacuum pump to set a distillation vessel target pressure within the distillation vessel and for operating the heat source to output heat at a heat source target temperature to heat the distillation vessel to a distillation vessel target temperature and boil the mixture in the distillation vessel at a user-selected distillation temperature and at a given heat flux.

At 245, a user input element is operatively coupled to the microcontroller for signalling the user-selected distillation temperature to the microcontroller. Operatively coupling the user input element may include operatively coupling a user input element enabling variable user-selected change of distillation temperature. In an example, a dial may be operatively coupled to microcontroller as the user input element.

A collector is coupled to the distillation vessel at 255 to receive solvent vaporized from any mixture of solvent and plant extract in the distillation vessel.

A mixture of solvent and plant extract is provided to the distillation vessel at 265 and an initial distillation temperature is selected at 275. In an example, the solvent may be an alcohol.

Heat is output from the heat source at 285 at a heat source initial target temperature to heat the distillation vessel to a distillation vessel initial target temperature and boil the mixture in the distillation vessel at the initial distillation temperature and an initial heat flux and initial distillation rate.

With a vacuum pump, a distillation vessel initial target pressure is set within the distillation vessel at 295. The distillation vessel initial target pressure may be determined from the selected initial distillation temperature.

The actions 205 to 295 are only illustrative and other alternatives can also be provided where one or more actions are added, one or more actions are removed, or one or more actions are provided in a different sequence without departing from the scope of the claims herein.

Figure 3:
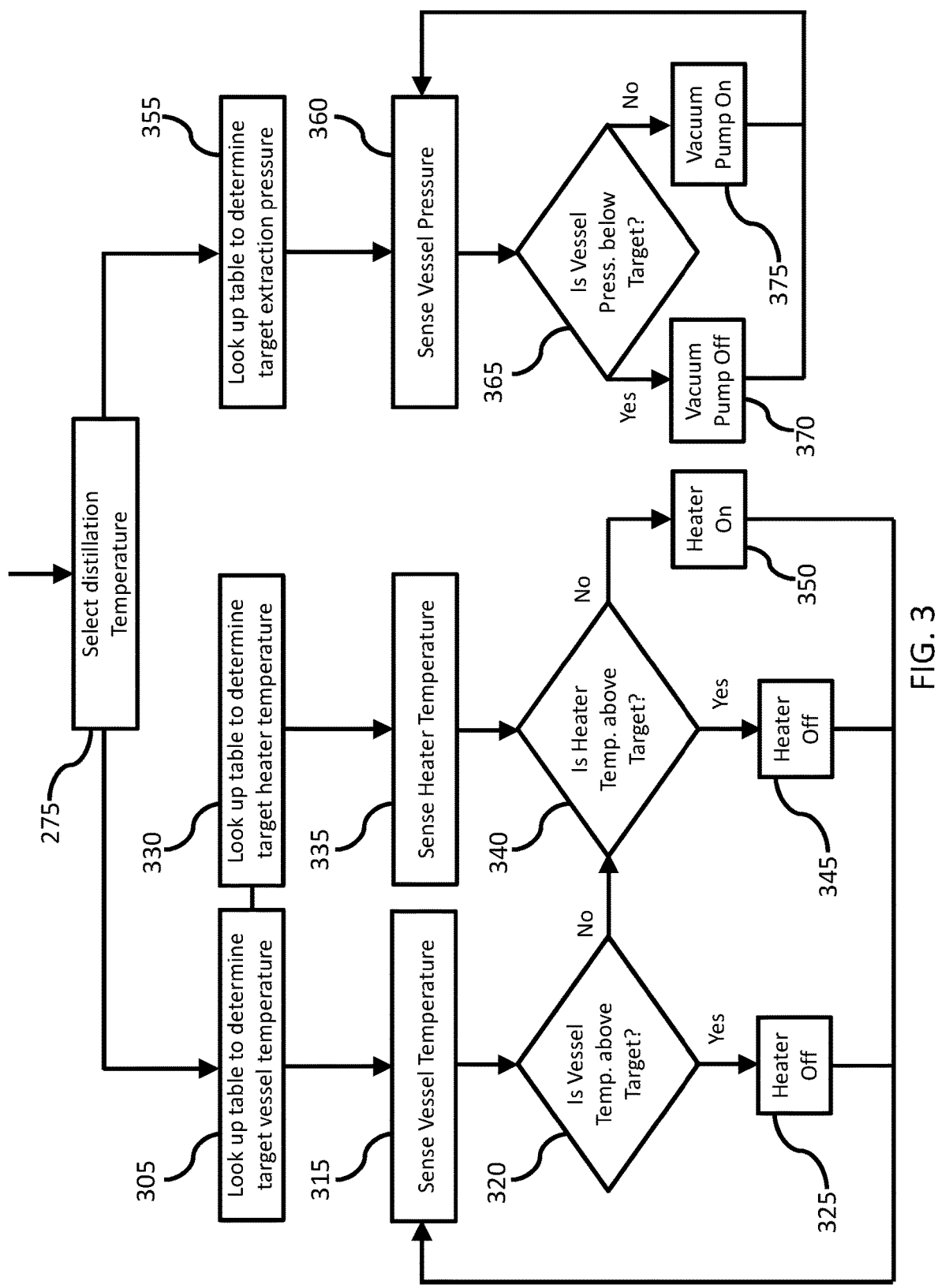
FIG. 3 illustrates a flow for an example method for regulating conditions of a system for controlling heat flux during phytochemical extraction.

FIG. 3 illustrates a flow for an example method for regulating conditions of a system for controlling heat flux during phytochemical extraction. In an example, outputting heat from the heat source as described above with reference to FIG. 2 further includes determining the heat source initial target temperature from the initial distillation temperature. In a further example, the heat source initial target temperature is returned, at 330, from one or more look-up tables relating heat source temperature to distillation temperature.

In another example, outputting heat from the heat source further includes first, determining the distillation vessel initial target temperature from the initial distillation temperature then determining the heat source initial target temperature from the distillation vessel initial target temperature. In a further example, (FIG. 3) outputting heat from the heat source further includes first, at 305, returning the distillation vessel initial target temperature from a look-up table relating distillation vessel temperature to distillation temperature then, at 330, returning the heat source initial target temperature from a look-up table relating heat source temperature to distillation vessel temperature.

In an example, setting the distillation vessel initial target pressure further includes determining the distillation vessel initial target pressure from the initial distillation temperature. In a further example, setting the distillation vessel initial target pressure further includes, at 355, returning the distillation vessel initial target pressure from a look-up table relating distillation vessel pressure to distillation temperature. In a still further example, the pressure within the distillation vessel is the pressure of the solvent at the desired maximum temperature which avoids eruptive boiling.

As mixture attains the desired temperature, the alcohol vaporizes and is removed from the vessel. Once initial target conditions are achieved, actual conditions are sensed and adjustments are made to maintain the target conditions. In an example control mode, temperature of the distillation vessel is sensed at 315 and when the sensed temperature of the distillation vessel is determined to be above the distillation vessel initial target temperature at 320, the heat source is turned off at 325.

Since a rapidly diminishing temperature difference between heat source and distillation vessel may reflect thermodynamic conditions unsuitable for phytochemical extraction, it may be useful to sense temperature at both the distillation vessel and the heat source.

In an example control action, temperature of the heat source is sensed at 335 and when the sensed temperature of the heat source is determined to be above the heat source initial target temperature at 340, the heat source is turned off at 345.

In another example control action, temperature of the distillation vessel is sensed at 315 and when the sensed temperature of the distillation vessel is determined at 320 to be equal to or below the distillation vessel initial target temperature, a further determination is made at 340 whether the heat source temperature is above the heat source initial target temperature. Temperature of the heat source is sensed at 335 and when the sensed temperature of the heat source is determined to be equal to or below the heat source initial target temperature at 340, the heat source is turned on at 350.

In another example control action, pressure of the distillation vessel may be sensed at 360 and when the sensed pressure of the distillation vessel is determined to be equal to or above the distillation vessel initial target pressure at 365, pressure is removed from the distillation vessel at 375.

As the mixture becomes thicker due to the increasing mass percentage of plant extracts, due to changes in the viscosity and chemical characteristics of the extract mixture superheating will increase to levels that cause local temperatures that exceed the maximum desired extract temperatures. The elevated temperatures can begin to degrade the extract.

A lower control temperature for the process may be selected. The system adjusts the vessel pressure downwards with the selected temperature to yield the new temperature. By combining a pressure change with the temperature change, the process can produce a similar heat flux and evaporation rate at the lower temperature. In an example, if the pressure alone were adjusted downward, the temperature of the liquid mixture would decrease as the control temperature of the heat input remained the same. This would increase the heat flux beyond the critical stable nucleate boiling regime and cause eruptive boiling and excessive local temperatures. If the temperature alone were reduced while maintaining a constant pressure, the heat flux into the vessel would decrease, thereby reducing the rate of distillation greatly or even stopping the process. The coordinated reduction or increase in temperature and pressure together in the system maintains a constant heat flux to promote the fastest rate of stable distillation possible while keeping superheated areas in the extract mixture below the desired maximum temperature.

When a modified distillation temperature different from the initial distillation temperature is selected at 275 (FIG. 2), heat is output from the heat source at a heat source modified target temperature to heat the distillation vessel to a distillation vessel modified target temperature and boil the mixture in the distillation vessel at the modified distillation temperature and the same initial heat flux. In an example, a microcontroller is configured to control the heat source to output heat at the heat source modified target temperature to heat the distillation vessel to the distillation vessel modified target temperature and boil the mixture in the distillation vessel at the modified distillation temperature and the initial distillation rate. Further, the microcontroller is configured to set a distillation vessel modified target pressure which avoids eruptive boiling.

In an example, when a modified distillation temperature is selected at 275, outputting heat from the heat source further includes determining the heat source modified target temperature from the vessel modified target temperature. In a further example determining the heat source modified target temperature further includes, at 330, returning the heat source modified target temperature from a look-up table relating heat source temperature to vessel temperature.

In an example, when a modified distillation temperature is selected at 275, outputting heat from the heat source further includes determining the distillation vessel modified target temperature from the modified distillation temperature. In a further example, determining the distillation vessel modified target temperature further includes, at 305, returning the distillation vessel modified target temperature from a look-up table relating distillation vessel temperature to distillation temperature.

In an example, when a modified distillation temperature is selected at 275, setting the distillation vessel modified target pressure within the distillation vessel further includes determining the distillation vessel modified target pressure from the modified distillation temperature. In a further example, when a modified distillation temperature is selected at 275, determining the distillation vessel modified target pressure further includes, at 355, returning the distillation vessel modified target pressure from a look-up table relating vessel pressure to the distillation temperature.

The microcontroller is configured to control the vacuum pump to set the distillation vessel modified target pressure within the distillation vessel.

In an example, pressure of the distillation vessel is sensed at 360 and pressure is removed from the distillation vessel at 375 when the sensed pressure of the distillation vessel is determined, at 365, to be equal to or above the distillation vessel modified target pressure.

In an example, temperature of the distillation vessel is sensed at 315 and the heat source is turned off at 325 when the sensed temperature of the distillation vessel is determined, at 320, to be above the modified distillation vessel target temperature.

In an example, temperature of heat source is sensed at 335 and the heat source is turned off at 345 when the sensed temperature of the heat source is determined, at 340, to be above the heat source modified target temperature.

In an example, temperature of the distillation vessel is sensed at 315 and it is determined whether the heat source is above target temperature at 340 when the sensed temperature of the distillation vessel is determined, at 320, to be equal to or below to the modified distillation vessel target temperature.

In an example, temperature of heat source is sensed at 335 and heat source is turned on at 350 when the sensed temperature of the heat source is determined, at 340, to be equal to or below the heat source modified target temperature.

In an example, pressure of the distillation vessel is sensed at 360 and pressure is maintained by turning the vacuum pump off at 370 when the sensed pressure of the distillation vessel is determined, at 365, to be below the distillation vessel modified target pressure.

The actions 305 to 375 are only illustrative and other alternatives can also be provided where one or more actions are added, one or more actions are removed, or one or more actions are provided in a different sequence without departing from the scope of the claims herein.

Figure 4:
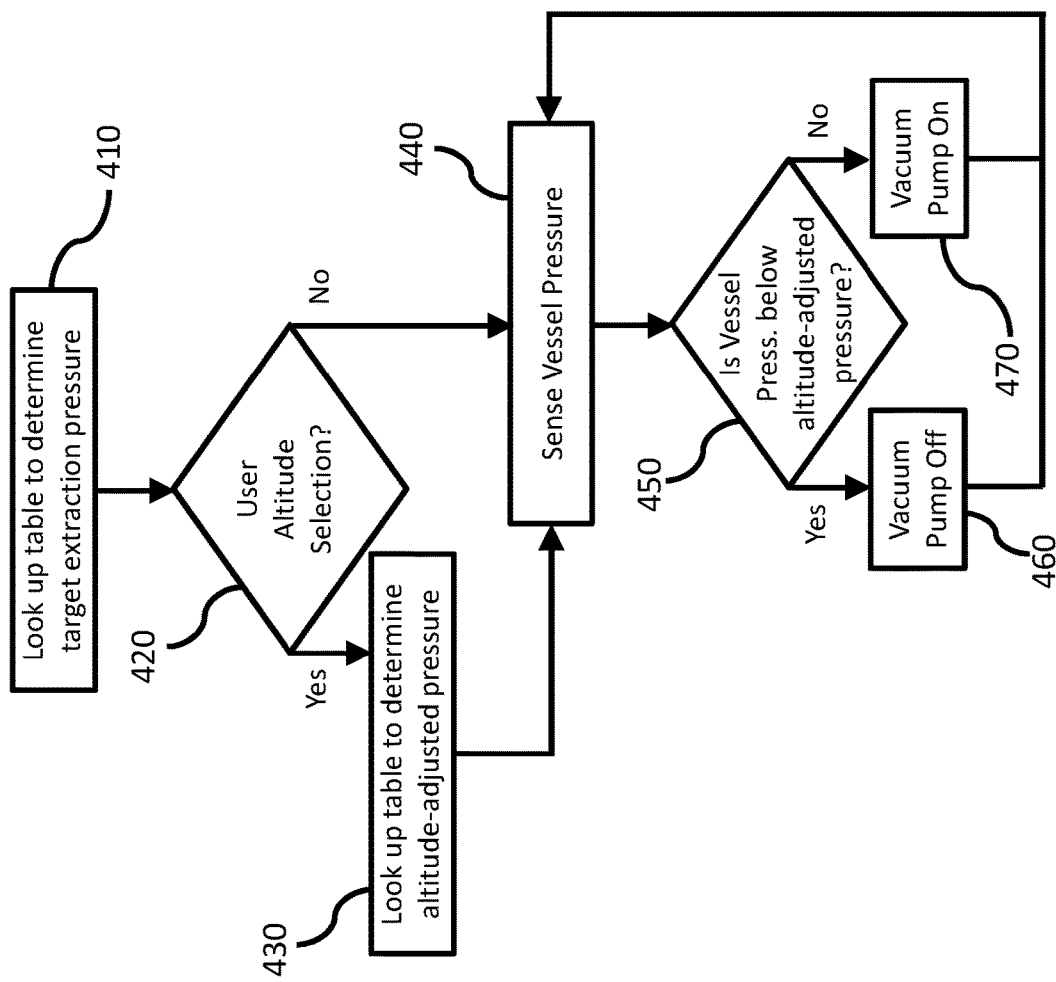
FIG. 4 illustrates a portion of a flow of an example adjusted method for regulating conditions of a system for controlling heat flux wherein pressure is tuned or adjusted based upon altitude.

In an embodiment, user tuning of pressure based upon altitude may be enabled by activating an altitude adjustment mode and selecting an altitude adjustment level. FIG. 4 illustrates a portion of a flow of an example adjusted method for regulating conditions of a system for controlling heat flux wherein pressure is tuned or adjusted based upon altitude.

After, at 410, the distillation vessel initial target pressure is returned from a look-up table relating distillation vessel pressure to distillation temperature it is determined whether user tuning of pressure has been enabled at 420. When an altitude adjustment mode has been activated and an altitude adjustment level has been selected, altitude-adjusted pressure is returned from a look-up table relating altitude adjusted pressure to distillation vessel pressure and vessel pressure is sensed at 440. While the altitude adjustment mode is inactive, no altitude-adjusted pressure is returned.

In an example, when the sensed pressure of the distillation vessel is determined, at 450, to be equal to or above the distillation vessel target pressure, pressure is removed from the distillation vessel at 470.

In an example, when the sensed pressure of the distillation vessel is determined, at 450, to be below the distillation vessel target pressure, pressure is maintained by turning the vacuum pump off at 460.

In an example accommodating user-tuning of pressure, when a modified distillation temperature is selected at 275, a microcontroller is configured to set a distillation vessel modified target pressure which avoids eruptive boiling.

After, at 410, the distillation vessel modified target pressure is returned from a look-up table relating distillation vessel pressure to distillation temperature it is determined whether user tuning of pressure has been enabled at 420. When an altitude adjustment mode has been activated and an altitude adjustment level has been selected, altitude-adjusted modified pressure is returned from a look-up table relating altitude adjusted pressure to distillation vessel pressure. While the altitude adjustment mode is inactive, no altitude-adjusted pressure is returned.

Continuing, vessel pressure is sensed at 440. When the sensed pressure of the distillation vessel is determined, at 450, to be equal to or above the distillation vessel modified target pressure, pressure is removed from the distillation vessel at 470. When the sensed pressure of the distillation vessel is determined, at 450, to be below the distillation vessel modified target pressure, pressure is maintained by turning the vacuum pump off at 460.

The actions 410 to 470 are only illustrative and other alternatives can also be provided where one or more actions are added, one or more actions are removed, or one or more actions are provided in a different sequence without departing from the scope of the claims herein.

Embodiments of the disclosure may also provide a computer program product that includes a non-transitory or non-transient computer-readable storage medium storing computer-executable code for controlling heat output from a heat source as well as distillation pressure in response to determinations made from sensor measurements and user temperature selection. The code, when executed, is configured to perform one or more of the actions 305 to 375 of the method as described in conjunction with FIG. 3 and/or one or more of the actions 410 to 470 of the method as described in conjunction with FIG. 4. As actions of the disclosed methods may be provided in different sequences, so the computer-executable code may be configured to provide a service having a different sequence of actions from those illustrated in FIGS. 3 and/or 4. In some examples, the code may be downloaded from a software application store, for example, from an "App store", to a data processing unit.

Embodiments of the present disclosure are susceptible to being used for various purposes, including, though not limited to, enabling users to modulate distillation temperature while maintaining an optimally high heat flux, process speed and critical nucleate boiling characteristic with variable feedstocks.

Modifications to embodiments of the present disclosure described in the foregoing are possible without departing from the scope of the present disclosure as defined by the accompanying claims. Expressions such as "including", "comprising", "incorporating", "consisting of", "have", "is" used to describe and claim the present disclosure are intended to be construed in a non-exclusive manner, namely allowing for items, components or elements not explicitly described also to be present. Reference to the singular is also to be construed to relate to the plural.

What is claimed is:

1. A method for phytochemical extraction, comprising:
providing a distillation vessel;
placing the distillation vessel on a heat source;
coupling the distillation vessel with a collector configured to collect condensed solvent;
providing a mixture of solvent and plant extract to the distillation vessel;
selecting an initial distillation temperature;
outputting heat from the heat source at a heat source initial target temperature to heat the distillation vessel to a distillation vessel initial target temperature and boil the mixture in the distillation vessel at the initial distillation temperature and at an initial heat flux and initial distillation rate;
with a vacuum pump, setting a distillation vessel initial target pressure within the distillation vessel;
selecting a modified distillation temperature different from the initial distillation temperature; and
changing the heat output from the heat source and the pressure set with the vacuum pump such that the mixture in the distillation vessel boils at the modified distillation temperature while maintaining the initial heat flux.

2. The method as set forth in claim 1, wherein outputting heat from the heat source further comprises determining the heat source initial target temperature from the initial distillation temperature.

3. The method as set forth in claim 1, wherein setting the distillation vessel initial target pressure further comprises determining the distillation vessel initial target pressure from the initial distillation temperature.

4. The method as set forth in claim 1, further comprising setting an altitude adjusted pressure determined from at least one of the distillation vessel initial target pressure and the initial distillation temperature.

5. The method as set forth in claim 1, further comprising sensing pressure of the distillation vessel and removing pressure from the distillation vessel with the vacuum pump when the sensed pressure of the distillation vessel is above the distillation vessel initial target pressure.

6. The method as set forth in claim 1, wherein changing the heat output from the heat source and the pressure set with the vacuum pump further comprises changing the heat output and the pressure such that the mixture in the distillation vessel at the modified distillation temperature while maintaining the initial distillation rate.

7. The method as set forth in claim 1, further comprising, with a microcontroller:
   controlling the outputting heat from the heat source; and
   controlling the setting the distillation vessel initial target pressure.

8. A method for phytochemical extraction, comprising:
   providing a distillation vessel;
   coupling the distillation vessel with a collector configured to collect condensed solvent;
   providing a mixture of solvent and plant extract to the distillation vessel;
   selecting an initial distillation temperature;
   outputting heat from a heat source at a heat source initial target temperature to heat the distillation vessel to a distillation vessel initial target temperature and boil the mixture in the distillation vessel at the initial distillation temperature and at an initial heat flux and initial distillation rate;
   with a vacuum pump, setting a distillation vessel initial target pressure within the distillation vessel;
   selecting a modified distillation temperature different from the initial distillation temperature; and
   changing the heat output from the heat source and the pressure set with the vacuum pump such that the mixture in the distillation vessel boils at the modified distillation temperature while maintaining the initial heat flux.

9. The method as set forth in claim 8, wherein outputting heat from the heat source further comprises determining the heat source initial target temperature from the initial distillation temperature.

10. The method as set forth in claim 8, wherein setting the distillation vessel initial target pressure further comprises determining the distillation vessel initial target pressure from the initial distillation temperature.

11. The method as set forth in claim 8, further comprising setting an altitude adjusted pressure determined from at least one of the distillation vessel initial target pressure and the initial distillation temperature.

12. The method as set forth in claim 8, further comprising sensing pressure of the distillation vessel and removing pressure from the distillation vessel with the vacuum pump when the sensed pressure of the distillation vessel is above the distillation vessel initial target pressure.

13. The method as set forth in claim 8, wherein changing the heat output from the heat source and the pressure set with the vacuum pump further comprises changing the heat output and pressure such that the mixture in the distillation vessel boils at the modified distillation temperature while maintaining the initial distillation rate.

14. The method as set forth in claim 8, further comprising, with a microcontroller:
   controlling the outputting heat from the heat source; and
   controlling the setting the distillation vessel initial target pressure.

15. A method for phytochemical extraction, comprising:
   providing a distillation vessel;
   coupling the distillation vessel with a heat source;
   coupling the distillation vessel with a collector configured to collect condensed solvent;
   providing a mixture of solvent and plant extract to the distillation vessel;
   selecting an initial distillation temperature;
   outputting heat from the heat source at a heat source initial target temperature to heat the distillation vessel to a distillation vessel initial target temperature and boil the mixture in the distillation vessel at the initial distillation temperature and at an initial heat flux and initial distillation rate;
   with a vacuum pump, setting a distillation vessel initial target pressure within the distillation vessel;
   selecting a modified distillation temperature different from the initial distillation temperature; and
   changing the heat output from the heat source and the pressure set with the vacuum pump such that the mixture in the distillation vessel boils at the modified distillation temperature without eruptive boiling.

16. The method as set forth in claim 15, wherein outputting heat from the heat source further comprises determining the heat source initial target temperature from the initial distillation temperature.

17. The method as set forth in claim 15, wherein setting the distillation vessel initial target pressure further comprises determining the distillation vessel initial target pressure from the initial distillation temperature.

18. The method as set forth in claim 15, further comprising setting an altitude adjusted pressure determined from at least one of the distillation vessel initial target pressure and the initial distillation temperature.

19. The method as set forth in claim 15, further comprising sensing pressure of the distillation vessel and removing pressure from the distillation vessel with the vacuum pump when the sensed pressure of the distillation vessel is above the distillation vessel initial target pressure.

20. The method as set forth in claim 15, wherein:
   changing the heat output from the heat source and the pressure set with the vacuum pump further comprises changing the heat output and the pressure such that the mixture in the distillation vessel boils at the modified distillation temperature while maintaining the initial heat flux.

21. The method as set forth in claim 15, further comprising, with a microcontroller:
   controlling the outputting heat from the heat source; and
   controlling the setting the distillation vessel initial target pressure.

* * * * *